United States Patent [19]

Strawn

[11] Patent Number: Plant 6,189

[45] Date of Patent: May 31, 1988

[54] MINIATURE ROSE PLANT

[76] Inventor: Leslie E. Strawn, 10422 Morningside Dr., Garden Grove, Calif. 92686

[21] Appl. No.: 879,791

[22] Filed: Jun. 20, 1986

[51] Int. Cl.[4] ..... A01H 5/00

[52] U.S. Cl. ..... Plt./8

[58] Field of Search ..... Plt./8

*Primary Examiner*—Robert E. Bagwill

[57] ABSTRACT

The subject of the present disclosure is a new and distinct variety of miniature rose plant characterized by creamy white and pale yellow buds and flowers of distinctive form and further indentified by the rounded dwarf, compact plant.

1 Drawing Sheet

1

The present invention relates to a new and distinct variety of hardy, dwarf, bush type rose plant of the miniature class; the variety being primarily characterized—as to novelty—by the creamy white and pale yellow buds and flowers which in general coloring effect are similar to Garden Party (Hybrid tea—U.S. Plant Pat. No. 1,814—expired).

The variety is further characterized by:

An abundance of bloom, with flowers borne one to a stem with an occasional side bud. Slightly fragrant.

A plant which is vigorous, of rounded, bushy growth habit, semi-glossy foliage with pointed leaflets; the buds and flowers being similar in form and size to Cupcake (Miniature—U.S. Plant Pat. No. 4,835).

The plant which has a normal height of 10 to 12 inches, can easily be maintained at lesser height by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between The Optimist (Floribunda—U.S. Plant Pat. No. 1,533 expired) as the seed parent and Darling Flame (Miniature—non-patented) as the pollen parent.

Subsequent to origination of the variety I successfully asexually reproduced it in my garden, located as foresaid, (also propagated by Pixie Treasures Rose Nursery, 4121 Prospect Ave., Yorba Linda, Orange County, Calif.) by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate indentifications being by reference to The British Colour Council Horticultural Colour Chart, except where common terms of color definition are employed.

Type: Hardy; dwarf; bushy; rounded; upright; seedling; greenhouse; outdoors; cut flowers; garden decoration; pot plant.

Class: Miniature.

*Variety name.*—Moon Mist.

*Generic name.*—Piximis.

2

Flowers borne: Singly on upright, slender stems; occasional side-bud.

Quanity of bloom: Abundant, both outdoors and in the greenhouse.

Bud:

*Peduncle.*—Medium length, 2½–3 cm; erect, straight, slender, sturdy; bronze or green; few glands; few hairs.

*Size.*—Before calyx breaks — 2 cm.

*Form.*—Pointed; foliaceous parts extend beyond tip of bud one third or more than its length.

*Color.*—Medium green. As calyx breaks — surface of guard petal may show streak of a color near Spinel red o23/1 from exposure.

Bloom:

*Size.*—When fully open — small, averaging 4½ to 5 cm.

*Petalage.*—Double, 38 to 40 petals, arranged symmetrically.

*Form.*—Ovoid. As petals open symmetrically they remain in their upright position, with topmost edges of petals flairing outward. When fully open outside petals reflex back at side edges.

Petals:

*Substance.*—Moderately thick and of good substance.

*Texture.*—Smooth and satiny on both surfaces. Slightly veined.

*Shape.*—Outside petal: Smooth edged. Broad; small point at apex. Pointed base. Width: approx. 2 cm. Intermediate petal: Not as large as outside petals. Width: approx 15 mm. Pointed base. Petaloids: Few close to stamens.

Color: One half to three quarters open flowers from plants grown outdoors at Pixie Treasures Rose Nursery, Yorba Linda, Calif., April 1986.

*Outside petal.*—Outside surface: Creamy white with tinge of color near to Spinel red o23/1 on outer edge. Center area may have streak or blotch of color near Spinel red o23/2. Base color near to pale Naples yellow 403/3. Inside surface: Creamy white, may have edges marked with a touch of a color near Spinel red o23/3. Center area — creamy white. Base — pale yellow near to Naples yellow 403/2.

*Intermediate petal.*—Outside surface: Outer and center areas — creamy white. Base color close to Naples yellow 403/2, carrying its coloring almost into center of petal. Inside surface: Same.

*Inside petal.*—Same as intermediate petals. Same base.

General color effect:

*Newly open flowers.*—Symmetrically arranged petals of creamy white with the pale yellow base color showing in its depths, and a slight evidence of red on the outer edges of some of the outside petals.

*Three to four days open.*—Keeps symmetry fully open with stamens showing. May or may not take on a blush of pink from exposure to sunlight in its final stages.

Behavior: Opens well in all weather. Petals tend to hang on for 5 to 6 days then fall, calyx remains and occasionally forms a hip.

*Flower longevity (April* 1986).—Plant in pot — 4 to 5 days; plant in ground — 5 to 6 days; cut flowers at living room temperature — 3 to 4 days.

Reproductive organs:

*Stamens.*—60 to 75; flairing outward.

*Filaments.*—Uneven lengths — 5 to 10 mm; pale yellow green.

*Anthers.*—Tan; introse.

*Pollen.*—Moderate amount.

*Pistils.*—Projects above disc.

*Styles.*—Several; tightly bunched; length — 5 mm; color — light red.

*Ovaries.*—Enclosed in calyx.

*Hips.*—Occasionally formed.

*Sepals.*—Permanent; spear shaped; reflexed.

*Seeds.*—Few if any.

Foliage:

*Leaves.*—Compound of five leaflets; length — 5 to 5½ cm; semi-glossy; moderate substance.

*Rachis.*—Length 2½ to 3 cm; upper side grooved; underside 2 or 3 soft thorns if any.

*Stipules.*—Smooth and small with short auricles flairing outward to 45 degrees.

*Color.*—Medium green leaflets with rachis green. Serrated edges of leaflets and veining — bronze on new foliage.

Growth:

*Habit.*—Dwarf; upright and rounded; height — 25 to 30 cm or 10 to 12 inches.

*Growth.*—Vigorous and steady; heavy bloomer; much branched with internodes spaced 2 to 3 cm.

*Canes.*—Slender; sturdy.

*Main stems.*—Dark green.

*Branches.*—Medium green.

*Thorns.*—Thornless.

*New shoots.*—Tinted bronze.

The following is claimed:

1. A new and distinct variety of miniature rose plant of hardy, dwarf, bushy, upright, rounded, much branched habit substantially as illustrated and described, characterized by buds and flowers which are in a color hue similar to Garden Party (Hybrid tea—U.S. Plant Pat. No. 1,814, expired) giving a coloring effect of creamy white with pale yellow undertones and resembling Cupcake (Miniature—U.S. Plant Pat. No. 4,835) in form and size; having buds and flowers of a distinct and unusual appearance as compared to other miniature rose plants; said flowers being fully double, unique in its ovoid form with high centers and further characterized by its vigor, abundant foliage and ease of propagation from soft wood cuttings and by budding, and with and abundance of flowers.

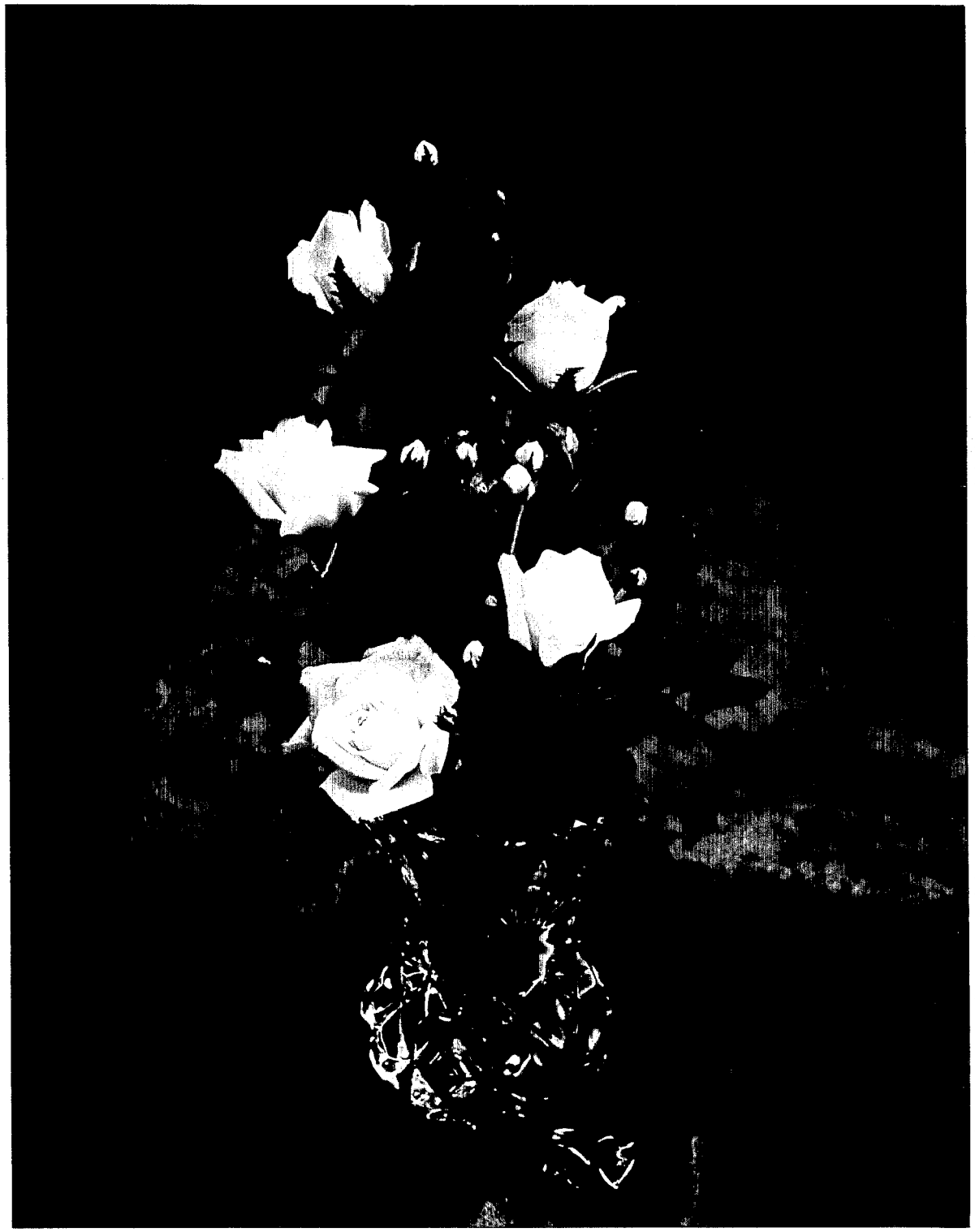

* * * * *